United States Patent [19]

Toepfer et al.

[11] Patent Number: 5,693,621

[45] Date of Patent: Dec. 2, 1997

[54] MALONIC ACID DERIVATIVES HAVING ANTIADHESIVE PROPERTIES

[75] Inventors: Alexander Toepfer, Hofheim; Gerhard Kretzschmar, Eschborn; Eckart Bartnik, Wiesbaden; Dirk Seiffge, Mainz-Kostheim, all of Germany

[73] Assignee: Hoechst Aktiengesellschaft, Frankfurt am Main, Germany

[21] Appl. No.: 403,525

[22] Filed: Mar. 13, 1995

[30] Foreign Application Priority Data

Mar. 11, 1994 [DE] Germany .................. 44 08 248.7
Aug. 25, 1994 [DE] Germany .................. 44 30 005.0

[51] Int. Cl.$^6$ .................. A61K 31/19; A61K 31/70; C07C 55/00; C07H 15/00
[52] U.S. Cl. .................. 514/25; 514/574; 536/4.1; 562/400; 562/590
[58] Field of Search .................. 536/4.1; 562/400, 562/590; 514/25, 574, 557

[56] References Cited

U.S. PATENT DOCUMENTS 5,079,353  1/1992  Ratcliffe et al. .................. 536/53
5,162,513  11/1992  Wong .................. 536/1.1

FOREIGN PATENT DOCUMENTS

WO 93/10796  of 0000  WIPO .
WO 92/00245  1/1992  WIPO .
WO 92/00251  1/1992  WIPO .
WO 92/09870  6/1992  WIPO .
WO 92/16640  10/1992  WIPO .
WO 92/18610  10/1992  WIPO .
0 536 394  4/1993  WIPO .

OTHER PUBLICATIONS

Ravindranath et al. "An Epitope Common to Gangliosides O–Acetyl–$G_{D3}$ and $G_{D3}$ Recognized by Antibodies . . . ", *Cancer Research*, 49:3891–3897 (1989).

Eckelman, Ed. "In Vivo Diagnosis and Therapy of Human Tumors with Monoclonal Antibodies", Proceedings of a Symposium held in Naples Italy, 16–19 Mar., 107–185 (1988).

Houghton et al. "Monoclonal Antibodies: Potential Applications to the Treatment of Cancer", *Seminars in Oncology*, 13:165–179 (1986).

Takada et al. "Enzymatic Preparation of Enantiomerically Pure (1R,2R)–and (1S,2S)–2–Aminocyclohexanols", *Bull. Chem. Soc. Jpn.*, 67:1196–1197 (1994).

Lowe et al. "ELAM–1–Dependent Cell Adhesion to Vascular Endothelium Determined by a Transfected Human Fucosyltransferase cDNA", *Cell*, 63:475–484 (1990).

Reutter et al. "Biological Significance of Sialic Acids", *Cell Biology Monographs*, 263–305 (1982).

*Primary Examiner*—Elli Peselev
*Attorney, Agent, or Firm*—Foley & Lardner

[57] ABSTRACT

The invention relates to malonic acid derivatives, which inhibit the binding of selectin to carbohydrate ligands, and pharmaceutical compositions and diagnostic agents containing these derivatives, and methods for using these pharmaceutical compositions and diagnostic agents.

20 Claims, No Drawings

MALONIC ACID DERIVATIVES HAVING ANTIADHESIVE PROPERTIES

BACKGROUND OF THE INVENTION

The present invention relates to malonic acid derivatives that inhibit cell adhesion involved in several pathological responses, and methods of producing such derivatives. The invention further relates to pharmaceutical compositions and diagnostic agents containing these derivatives, and methods using these pharmaceutical compositions and diagnostic agents.

Endothelial cells and various circulating cells of the hematolymphoid system express unique surface glycoproteins known as selectins, which mediate intercellular adhesion. (K.-A. Karlsson, TIPS 12: 265-272 (1991)). Intercellular adhesion plays an important role in many pathological responses. For example, the adherence of platelets and leukocytes to vascular surfaces is a critical component of the inflammatory response and is part of a complex series of reactions involving the simultaneous and interrelated activation of the complement, coagulation and immune systems. In addition, leukocyte adherence to vascular endothelium is a key initial step in the migration of leukocytes to tissues in response to microbial invasion.

Compounds that block this initial adhesive interaction are thus expected to have efficacy in the treatment of inflammatory diseases such as rheumatoid arthritis, asthma, and psoriasis. Other indications include adult respiratory distress syndrome, reperfusion injury, ischemia, ulcerative colitis, vasculitis, atherosclerosis, and inflammatory bowel disease. (Boschelli et al., U.S. Pat. No. 5,356,926). Synthetic analogs (mimetics) of carbohydrate ligands that bind specifically to selectins, and thus inhibit selectin-mediated intercellular adhesion, have been implicated as promising therapeutics as anti-inflammatories and anti-coagulants (T. A. Springer, L. A. Lasky, Nature 349: 196-197 (1991); T. Feizi, TIBS 16: 84-86 (1991)).

In addition, carbohydrate ligands are involved in bacterial and viral infections and cancer. Carbohydrate ligands are recognition domains for viruses (J. C. Paulson, The Receptors, Vol. II, P. M. Conn, ed., Academic Press, 131 (1985)), bacteria (Strömberg et al., EMBO J. 9: 2001 (1990)) and toxins (Karlsson et al., Sourcebook of Bacterial Protein Toxins, J. E. Alouf, J. H. Freer, eds., Academic Press, 56: 3537 (1990)). Carbohydrate mimetics are thus expected to have efficacy in the prevention and treatment of bacterial and viral infections and sepsis.

Cancer cells express carbohydrate ligands in patterns different from those in normal cells. Carbohydrate mimetics could be used to generate antibodies that recognize the naturally occurring carbohydrate ligands and thus facilitate the diagnosis of cancer. Because leukocyte adherence to vascular endothelium is also relevant to tumor cell metastasis, synthetic analogs that inhibit selectin-mediated intercellular adhesion are expected to have efficacy in the treatment of metastatic conditions. (S.-i. Hakomori, Cancer Cells, Vol. 3, No. 12 (December 1991)).

With regard to selectin-mediated intercellular adhesion, silylated and fucosylated carbohydrate ligands, specifically sialyl-Lewis-X[αNeu5Ac(2→3)βGal(1→4)[αFuc(1→3)]-βGlcNAc-OR] and sialyl-Lewis-A [αNeu5Ac(2→3)βGal(1→3)[αFuc(1→4)]-βGlcNAc-OR] (where R is defined as an aglycone having at least one carbon atom), are particularly important. (Schauer, ed., "Sialic Acids" in Cell Biology Monographs, Vol. 10 (1982); Lowe et al., Cell, 63: 475-485 (1990)). Both chemical (Ratcliff et al., U.S. Pat. No. 5,079, 353) and chemical/enzymatic (A. Venot et al., PCT/CA 92/00251) syntheses of these compounds have been developed. These processes, however, are highly complex.

Therefore, research is presently underway to develop analogs that are easier to synthesize, but have equal or greater selectin binding affinity, than the naturally occurring carbohydrate ligands. Toward this end, several analogs, containing particular residue substitutions, have been synthesized. For example, neuraminic acid was replaced by lactic or glycolic acid, fucose was replaced by glycerol or trifluoromethylfucose, and N-acetylglycosamine was replaced by glycosamine or glucose (PCT/US 92/09870). Substitution of neuraminic acid by sulfate or phosphate has likewise been described (PCT/CA 92/00245). In addition, the replacement of glucosamine with a chain of at least 2 carbon atoms has been described (WO 92/18610).

To date, an efficient, enzymatic large-scale synthesis has been developed only for native sialyl-Lewis-X and sialyl-Lewis-A having slight modifications (C. H. Wong et al., WO 92/16640 and U.S. Pat. No. 5,162,513). These analogs, however, have the disadvantages of both a low affinity for corresponding selectins and a low in vivo stability (active substances are not orally available).

SUMMARY OF THE INVENTION

Accordingly, an object of the present invention is the economical and simple synthesis of malonic acid derivative analogs that are highly stable physiologically and that have greater selectin binding affinity than their naturally occurring carbohydrate ligand counterparts. It is a further object of the present invention to use these malonic acid derivative analogs to produce pharmaceutical compositions and diagnostic agents capable of diagnosing, preventing or treating bacterial or viral infections, tumor cell metastasis, and inflammatory pathologies.

These objectives are achieved by a compound of formula I

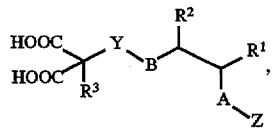

in which $R^1$, $R^2$ and $R^3$ independently of one another are H, $(CH_2)_m X$ or $CH_2O(CH_2)_m X^1$ or $R^1$ and $R^2$ together form a six-membered carbo- or heterocycle having at least one substituent selected from the group consisting of $R^4$, $R^5$ and $R^6$ and A and B independently of one another are O, S, NH, HN—CO, OC—NH, O—CO, OC—O, NH—CO—O, O—CO—NH, S—CO, SC—O, O—CS—S, S—CS—O, NH—CS—S, S—CS—NH or $CH_2$ and Z is a pyranose, a furanose, an open-chain polyalcohol or $Y-X^6$, Y is $-O-(CX^2X^3)_n-$, $-(CX^2X^3)_n$, $-(CX^2R^7)_n-$, $-(CR^7R^8)_n-$, $-CH_2-(CX^2X^3)-_n$ or a saturated or unsaturated, six-membered carbo- or heterocycle having at least one substituent $R^9$ or a combination of the chain $-O-(CX^2X^3)_n$, $-(CX^2X^3)_n$, $-(CX^2R^7)_n-$, $-(CR^7R^8)_n-$ and the carbo- or heterocycle, where $R^4$, $R^5$ and $R^6$ independently of one another are H, OH, $(CH_2)_q X^4$, $CH_2O(CH_2)_q X^5$ or $HNC(O)CH_3$ and $R^7$, $R^8$ and $R^9$ independently of one another are H, OH, $-O-(CH_2)_q X^4$ or $CH_2O(CH_2)_q X^5$ and X, $X^1$, $X^2$, $X^3$, $X^4$ and $X^5$ independently of one another are H, $NH_2$, COOH, OH, $CH_2OH$, $CH_2NH_2$, $C_1-C_{20}$-alkyl or $C_6-C_{10}$-aryl and $X^6$ is OH or

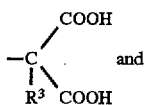

m, n and q independently of one another are integers from 1 to 20.

The objectives set forth are further achieved by a method for producing a compound of formula I according to the invention, comprising the steps of:

(1) alkylating, acylating or glycosylating a functional group of an acceptor II

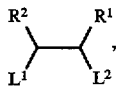    II containing at least two adjacent functional groups $L^1$ and $L^2$ and containing the substituents $R^1$ and $R^2$, with one equivalent of a donor III bearing at least two functional groups $L^3$ and $L^4$

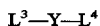    III, one functional group $L^3$ of which is protected, if necessary, and the other functional group $L^4$ of which is optionally present in activated form, to achieve intermediate compound IV;

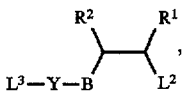    IV (2) alkylating, acylating or glycosylating the unprotected functional group $L^2$ of intermediate compound IV, with donor V having an activated functional group $L^5$

    V, wherein the other functional groups may carry protective groups, if necessary, to achieve intermediate compound VI;

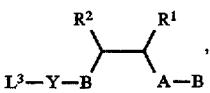    VI (3) selectively deprotecting and activating the functional group $L^3$ by reaction of intermediate compound VI with a malonic acid derivative and (4) removing all protective groups to achieve a compound of formula I according to the invention, wherein $R^1$, $R^2$, Y, B, Z and A are as defined above.

The objectives set forth are further achieved by pharmaceutical compositions prepared from compounds of formula I according to the invention, and the use of these pharmaceutical compositions in effective therapeutic amounts to prevent or treat bacterial or viral infections, tumor cell metastasis, and inflammation pathologies.

A further embodiment of this invention provides pharmaceutical compositions for inhibiting the binding of a selectin to a carbohydrate ligand on a cell expressing a carbohydrate ligand, in which the composition comprises the above compound of formula I in a pharmaceutically acceptable carrier.

Yet another embodiment provides methods of inhibiting the binding of a selectin to a carbohydrate ligand on a cell expressing said carbohydrate ligand, in which a therapeutically effective dose of the pharmaceutical composition according to the invention is administered to a subject.

Other embodiments provide an antibody against a compound of formula I and diagnostic kits for detecting a carbohydrate ligand that binds to a selectin.

Other embodiments provide methods of detecting a selectin-expressing cell by contacting a sample suspected of containing said selectin-expressing cell with a compound of formula I according to the invention that is detectably labeled, and then detecting the binding of the selectin-expressing cell with the detectably labeled compound.

Still other embodiments provide methods of detecting in a sample a carbohydrate ligand by contacting a sample suspected of containing a carbohydrate ligand-expressing cell with a detectably labeled antibody according to the invention and then detecting the binding of the carbohydrate ligand-expressing cell with the detectably labeled antibody.

DETAILED DESCRIPTION OF PREFERRED EMBODIMENTS

Thus, one embodiment of the present invention relates to a compound that is a malonic acid derivative.

1. In a preferred embodiment, the compound is a compound of formula I

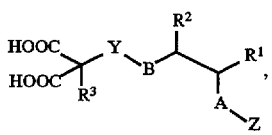    I in which $R^1$, $R^2$ and $R^3$ independently of one another are H, $(CH_2)_m X$ or $CH_2O(CH_2)_m X^1$ or $R^1$ and $R^2$ together form a six-membered carbo- or heterocycle having at least one substituent selected from the group consisting of $R^4$, $R^5$ and $R^6$ and A and B independently of one another are O, S, NH, HN—CO, OC—NH, O—CO, OC—O, NH—CO—O, O—CO—NH, S—CO, SC—O, O—CS—S, S—CS—O, NH—CS—S, S—CS—NH or $CH_2$ and Z is a pyranose, a furanose, an open-chain polyalcohol or $Y-X^6$, Y is $-O-(CX^2C^3)_n$, $-(CX^2X^3)_n-$, $-(CX^2R^7)_n-$, $-(CR^7R^8)_n-$, $-CH_2-(CX^2X^3)-_n$ or a saturated or unsaturated, six-membered carbo- or heterocycle having at least one substituent $R^9$ or a combination of the chain $-O-(CX^2X^3)_n$, $-(CX^2X^3)_n$, $-(CX^2R^7)_n-$, $-(CR^7R^8)_n-$ and the carbo- or heterocycle, where $R^4$, $R^5$ and $R^6$ independently of one another are H, OH, $(CH_2)_q X^4$, $CH_2O(CH_2)_q X^5$ or $HNC(O)C_3$ and $R^7$, $R^8$ and $R^9$ independently of one another are H, OH, $-O-(CH_2)_q X^4$ or $CH_2O(CH_2)_q X^5$ and X, $X^1$, $X^2$, $X^3$, $X^4$ and $X^5$ independently of one another are H, $NH_2$, COOH, OH, $CH_2OH$, $CH_2NH_2$, $C_1$–$C_{20}$-alkyl or $C_6$–$C_{10}$-aryl and $X^6$ is OH or

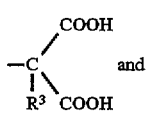

m, n and q independently of one another are integers from 1 to 20,

2. In a preferred embodiment, the compound of formula I is defined such that $R^1$ and $R^2$ form a six-membered carbocycle and
$R^3$, $R^4$, $R^5$ and $R^6$ are H,
A is O,
Z is a -fucopyranosyl group,
Y is $(CX^2X^3)_n$ and
$X^2$ and $X^3$ are H, 3. Advantageously, in the foregoing compounds, B is O. Other preferred compounds include:
4. those wherein n is 3, namely

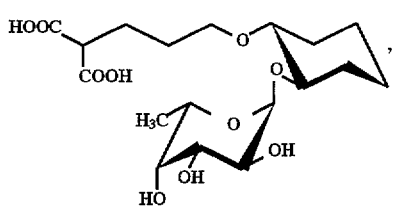
(7b)

5. those wherein n is 4, namely

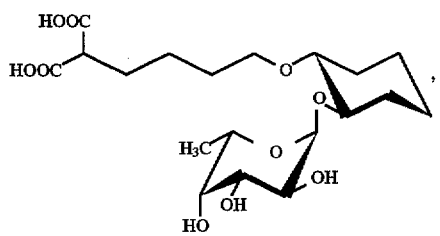
(7c)

6. and those wherein n is 5, namely

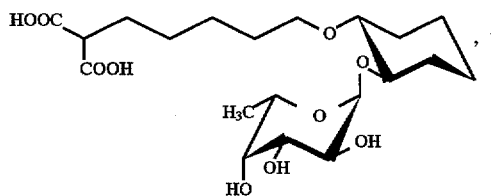
(7a)

7. Yet another preferred compound is defined such that B is HNCO—O.
8. In another preferred embodiment, n is 4, namely

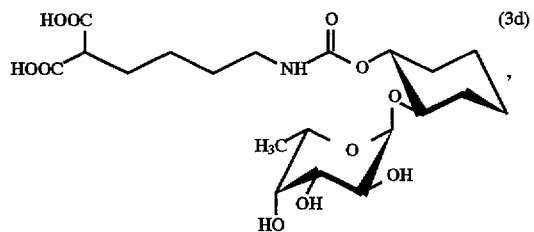
(3d)

9. Yet other preferred compounds as in formula I are defined in that
$R^1$ and $R^2$ form a six-membered carbocycle and
$R^3$, $R^4$, $R^5$ and $R^6$ are H,
A and B are O,
Z is a -fucopyranosyl group,
Y is a combination of a chain —O—$(CX^2X^3)_n$ and a heterocycle, where
$X^2$ and $X^3$ are H, 10. Preferably, the heterocycle is a galactosyl radical and n is 2, namely

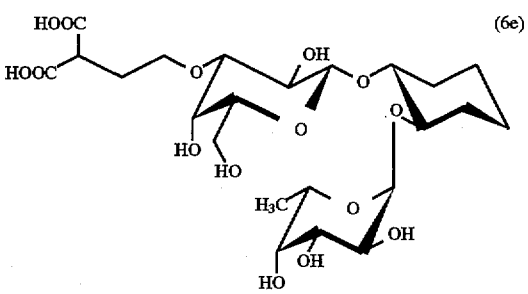
(6e)

11. In another embodiment, a compound of formula I is distinguished in that $R^1$ and $R^2$ together form a substituted tetrahydropyran ring, and
A and B are O,
Z is a -fucopyranosyl group,
Y is $(CX^2,X^3)_n$, where
$R^3$, $X^2$ and $X^3$ are H and n is 4, 12. In another embodiment, the substituents of the tetrahydropyran ring $R^4$ and $R^5$ are H and the substituent in the tetrahydropyran ring between the ring heteroatom O and the ring substituent —A—Z
$R^6$ is $CH_2O(CH_2)_qX^5$ and
$X^5$ is $C_6H_5$, 13. In a preferred embodiment, q is 4, namely

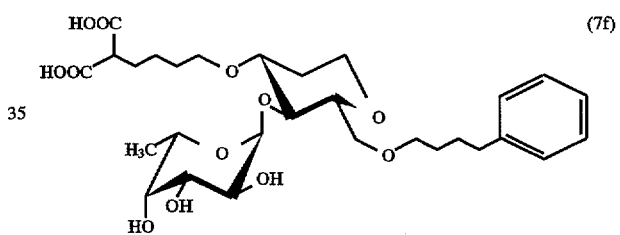
(7f)

14. Another preferred compound of formula I as in No. 11 is distinguished in that the tetrahydropyran ring is a pyranose.

15. Preferably, such compound comprises an N-acetyl-D-glucosamine.

16. Another preferred compound is of formula I wherein $R^1$ and $R^2$ together form a six-membered carbocycle, A-Z is

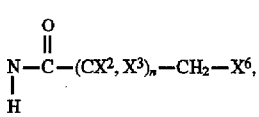

-B-Y is

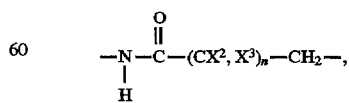

$R^3$ and $X^2$ are H,
$X^3$ and $X^6$ are OH and
n is 4,

17. Alternatively $X^6$ preferably is

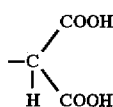

The compounds according to the invention can be prepared from commercially available components containing at least 2 adjacent functional groups such as (1R,2R)-trans-1,2-cyclohexanediol (Fluka), trans-2-aminohexanol (enantiomer separation: Takada H. et al., *Bull. Chem. Soc. Jpn.* 67 (4) 1196–97 (1994)) or trans-1,2-cyclohexanediamine. The corresponding monoalkylated compounds, e.g., monallylated diol, can be synthesized from these compounds. Alternatively, a linkage (amide, ester, amine, thioether, thioester, urethane, xanthate or dithiocarbamate) other than the ether bond can be selected. The second functional group is then glycosylated using an activated monosaccharide component, e.g., thioethyl-O-2,3, 4-tri-O-benzyl-β-L-fucopyranoside or O-{2,3,4,6-tetra-O-benzyl-α/β-D-mannopyranosyl} trichloroacetimidate. Instead of a monosaccharide, a polyalcohol such as L-threitol can also be linked (via 1,2,3-tri-O-benzyl-4-O-p-toluenesulfonate). In this way a compound without a glycosidic bond is obtained. After removal of the allyl protective group (or another suitable protective group) of the monoallylated tosylate initially linked, the liberated hydroxyl group is tosylated, for example, and then alkylated using dimethyl malonate (or dibenzyl malonate). Hydrogenolysis (and hydrolysis) yields the desired malonic acid derivative.

The compounds of formula I also can be prepared from commercially available compounds containing at least two adjacent functional groups such as (1R,2R)-trans-1,2-cyclohexanediamine, which upon reaction with two equivalents of glucono-1,5-lactone gives an intermediate compound bearing two identical side chains each having a primary and several secondary OH groups and capable of yielding the desired malonic acid derivative after selective protection and activation according to known methods, e.g., tritylation, benzylation, detritylation and tosylation, using dimethyl malonate. In addition, an appropriate variation of the protective group technique and appropriate activation of the primary OH groups of both side chains, result in a compound bearing two malonic acid groups, with each of the side chains having a terminal malonic acid group.

Thus, the compound of formula I according to the invention is prepared by the method comprising the steps of (1) alkylating, acylating or glycosylating a functional group of an acceptor II

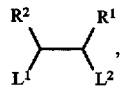 II containing at least two adjacent functional groups $L^1$ and $L^2$ and containing the substituents $R^1$ and $R^2$, with one equivalent of a donor III bearing at least two functional groups $L^3$ and $L^4$

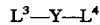 III, one functional group $L^3$ of which is protected, if necessary, and the other functional group $L^4$ of which is optionally present in activated form, to achieve intermediate compound IV;

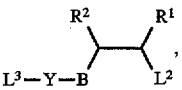 IV (2) alkylating, acylating or glycosylating the unprotected functional group $L^2$ of intermediate compound IV, with donor V having an activated functional group $L^5$

 V, wherein the other functional groups may carry protective groups, if necessary, to achieve intermediate compound VI;

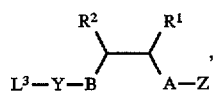 VI (3) selectively deprotecting and activating the functional group $L^3$ by reaction of intermediate compound VI with a malonic acid derivative and (4) removing all protective groups to achieve a compound of formula I according to the invention, the variables $R^1$, $R^2$, Y, B, Z and A having the meaning mentioned in the invention.

Alternatively acceptor II can first be reacted with donor V and then with donor III to give the intermediate compound VI.

Preferably the compounds as in No. 3, for example the compounds 7a, 7b and 7c, are prepared by employing (1R,2R)-trans-1,2-cyclohexanediol as acceptor II, an n-allyloxy-1-p-toluenesulfonyloxy-($C_2$-$C_n$)-alkane as donor III and thioethyl-O-2,3,4-tri-O-benzyl-β-L-fucopyranoside as donor V.

A compound as in No. 7, for example compound 3d, preferably can be prepared using the process according to the invention, wherein acceptor II is first reacted with donor V and then with donor III to give the intermediate compound VI by using (1R,2R)-trans-1,2-cyclohexanediol as acceptor II, an aminoalkanol activated with p-nitrophenyl chloroformate as donor III and thioethyl-O-2,3,4-tri-O-benzyl-β-L-fucopyranoside as donor V.

The compound described in No. 16 preferably can be prepared using the process according to the invention by using (1R,2R)-trans-1,2-cyclohexanediamine as acceptor II and glucono-1,5-lactone as donors III and V.

The compound described in No. 17 preferably can be prepared using the process according to the invention by using (1R,2R)-trans-1,2-cyclohexanediamine as acceptor II, glucono-1,5-lactone as donors III and V and by reacting intermediate compound VI with two equivalents of an appropriate malonic acid derivative after selective deprotection and activation of the terminal functional groups on Y and Z in each case.

Despite their substantially lower molecular weight, the malonic acid derivatives according to the invention can have a higher selectin binding affinity than their naturally occurring carbohydrate ligand counterparts. The cell adhesion assays described below demonstrate this higher affinity.

Wells of a 96-well microtiter test plates (Nunc Maxisorb) were pretreated at room temperature for 2 hours with 100 μl of a goat anti-human IgG antibody (Sigma) diluted (1:100) in 50 mM tris pH 9.5. The antibody solution was removed, and the wells were washed once with PBS. Blocking buffer (0.1% gelatin, 1% BSA, 5% calf serum, 0.2 mM PMSF, 0.02% sodium azide) was added (150 μl per well) and left at room temperature for 1 hour. The blocking buffer was removed, and the wells were washed once with PBS. Cell culture supernatant from appropriately transfected and expressed COS cells were pipetted into the wells (100 µl per well) and incubated at room temperature for 2 hours. The cell culture supernatant was removed, and the wells were washed once with PBS. Binding buffer (50 mM HEPES, pH 7.5; 100 mM NaCl; 1 mg/ml BSA; 2 mM $MgCl_2$; 1 mM $CaCl_2$; 3 mM $MnCl_2$; 0.02% sodium azide, 0.2 mM PMSF) was added (20 µl per well). The test sample (5 µl per well) was added, and the wells were mixed by swirling the plates and incubated at room temperature for 10 minutes.

Fifty ml of an HL60 cell culture containing 200,000 cells/ml were centrifuged at 350 g for 4 minutes. The pellet was resuspended in 10 ml of RPMI 1640, and the cells were centrifuged again. To label the cells, 50 µl of BCECF-AM (Molecular Probes) were dissolved in 5 µl of anhydrous DMSO; 1.5 ml of RPMI 1640 were then added to the BCECF-AM/DMSO solution. The cells were resuspended using this solution and incubated at 37° C. for 30 minutes. After centrifugation at 350 g for two minutes, the labeled cell pellet was resuspended in 11 ml of binding buffer, and the resuspended cells were divided into 100 µl aliquots in the microtiter plate wells. The plate was allowed to stand at room temperature for 10 minutes to allow the cells to sediment on the bottom of the test plate, and thus have the chance to adhere to the coated plastic.

The assay was stopped by immersing the microtiter plate completely at an angle of 45° in the stop buffer (25 mM tris, pH 7.5; 125 mM NaCl; 0.1% BSA; 2 mM $MgCl_2$; 1 mM $CaCl_2$; 3 mM $MnCl_2$; 0.02% sodium azide). The stop buffer was removed from the wells by inversion, and the procedure was repeated twice more. The amount of BCECF-AM-labeled cells firmly adhering in the wells was quantified by a cytofluorimeter (Millipore), at a sensitivity setting of 4, an excitation wavelength of 485/220 nm and an emission wavelength of 530/250 nm.

Based upon the results of the above described assay, the present inventors determined that the IC 50 values for E-selectin [mM] and P-selectin [mM] (in parentheses) were as follows:

---

5-Malonyl-1-hydroxypentyl-(1→1)-[α-L-fucopyranosyl)-(1→2)]-(1R,2R)-trans-1,2-cyclohexanediol (7a):
      0.7–1.1      (0.32–0.43)
(The values for sialyl-Lewis X are somewhat higher for E-selectin and even distinctly higher for P-selectin (in each case 2 mmol) and are thus poorer.)
4-Malonyl-1-hydroxybutyl-(1→1)-[α-L-fucopyranosyl)-(1→2)]-(1R,2R)-trans-1,2-cyclohexanediol (7c):
      not measurable      (0.175)
4-Malonyl-1-amininocarbonylbutyl-(4→2)-[(α-L-fucopyranosyl)-(1→1)]-(1R,2R)-trans-1,2-cyclohexanediol (3d):
      greater than 1      (0.0065)
(1R,2R)-trans-1,2-Cyclohexanediol-O-(α-L-fucopyranosyl)-β-D-2-O-malonylethylgalactopyranoside (6e):
      1.4      (0.018)
4-Malonyl-1-hydroxybutyl-(1→3)-[(α-L-fucopyranosyl)-(→4)]-[4-phenyl-1-hydroxybutyl-(1→6)]-1,2-didesoxyglucose (7f):
      0.34      (0.017)

---

Selectins are unique glycoproteins expressed on endothelial and hematolymphoid cell surfaces that mediate intercellular adhesion. (Springer, Nature, 346: 425 (1989), which is herein incorporated by reference). Intercellular adhesion is involved in many pathological responses. For example, intercellular adhesion is a prerequisite for the movement of leukocytes from the blood to tissue sites where immune reactions and inflammation occur. By "inflammation" is meant reactions of both the specific and non-specific defense systems. A specific defense system reaction is a specific immune system reaction to an antigen. Examples of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils.

The malonic acid derivatives according to the present invention are all carbohydrate ligand mimetics specific for the known selectins. Accordingly, these derivatives can inhibit the binding of selectins to their naturally occurring carbohydrate ligand counterparts, and thus inhibit intercellular adhesion. A ligand mimetic is a molecule that conformationally and functionally serves as a substitute for the natural ligand recognized by a selectin receptor.

Thus, in one embodiment, the invention relates to pharmaceutical compositions for inhibiting the binding of a selectin to a carbohydrate ligand on a cell expressing such a carbohydrate ligand. By the term "cell expressing carbohydrate ligand" is meant that a selectin-specific carbohydrate ligand is produced by cells associated with a specific condition and that production can be detected by any known method, for instance, by direct assays of mRNA transcript. Such cells include but are not limited to bacteria, viruses, white blood cells and cancer cells. White blood cells include but are not limited to leukocytes, lymphocytes and neutrophils. Cancer cells include but are not limited to those cells associated with colorectal, breast, ovarian and prostate cancer.

The pharmaceutical compositions according to the invention are prepared by bringing a malonic acid derivative according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

In another embodiment, the invention relates to a method of inhibiting the binding of a selectin to a carbohydrate ligand on a cell expressing such a carbohydrate ligand. This method involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, flidants or lubricants, flavorings, sweeteners or solubilizers are customarily used as described above. The pharmaceutical compositions are suitable for use in a variety of drug delivery systems. For a brief review of present methods for drug delivery, see Langer, *Science*, 249: 1527–1533 (1990), which is incorporated herein by reference.

The pharmaceutical compositions according to the invention may be administered locally or systemically to control tissue damage associated with selectin-mediated injuries. Moreover, because of the specificity of such derivatives for sites of inflammation, these compositions will be more effective and less likely to cause complications when compared to traditional anti-inflammatory agents. In the case of influenza therapy, the pharmaceutical compositions can inhibit the binding of viruses to the neuraminic acid on the surface of target cells and thus prevent the endocytosis of the virus particle. Other treatable selectin-mediated diseases include autoimmune diseases (e.g., rheumatoid arthritis, multiple sclerosis, inflammatory bone disorders, lupus, myastheniagravis, allergies, osteoarthritis, asthma, contact dermatitis, psoriasis, adult respiratory distress syndrome, and transplant rejection), infections (e.g., rhinitis, influenza, Helicobacter pylori infection, malaria, and septic shock), cancers (e.g., colorectal, breast, ovaries, and prostate), central nervous system disorders (e.g., stroke, trauma), reperfusion injuries (e.g., myocardial infarct, angioplasty, unstable angina, and systemic shock), and osteoporosis, wounds and severe burns.

By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) Goodman and Gilman's: *The Pharmacological Bases of Therapeutics*, 8th ed., Pergamon Press; and *Remington's Pharmaceutical Sciences*, 17th ed. (1990), Mack Publishing Co., Easton, Pa., each of which is herein incorporated by reference.

In another embodiment, the present invention relates to an antibody. The term "antibody" refers to both poly- and monoclonal antibodies and fragments thereof. Indeed, the compounds according to the present invention are suitable for the production of antibodies for the diagnostic determination of ligands which are not accessible, not immunogenic enough or unknown. In many autoimmune disorders and tumors, certain ligands or antigens on the cell membrane are highly regulated. However, these are frequently unknown, cannot be isolated in pure form or are not sufficiently immunogenic to be able to produce antibodies therefrom. The compounds according to the present invention can be used for the production of antibodies that cross-react with epitopes of the natural, unknown or inaccessible ligands.

Polyclonal antibodies against the compounds of the present invention can be produced in various ways using techniques well-understood by those having ordinary skill in the art. Details of these techniques are described in "Production of Polyclonal Antisera in Rabbits, Rats, Mice and Hamsters" in *Current Protocols in Immunology*, Coligan, J. E., et al., eds., National Institutes of Health, section 2.4.1 (1992), which is hereby incorporated by reference.

Monoclonal antibodies against the compounds of the present invention can be produced in various ways using techniques well-understood by those having ordinary skill in the art. Details of these techniques are described in *Antibodies: A Laboratory Manual*, Harlow et al. Cold Spring Harbor Publications, p. 726 (1988), which is hereby incorporated by reference. The monoclonal antibodies according to this invention are multiplied according to in vitro and in vivo methods well-known in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention may also be obtained by multiplying hybridoma cells in vivo. Cell clones are injected into mammals which are histocompatible with the parent cells, e.g. syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the mammal.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer as supplied by Applied Biosystems, Multiple Peptide Systems, etc., or they may be produced manually, using techniques well known in the art. See Geysen, et al. *J. Immunol. Methods* 102: 259–274 (1978), hereby incorporated by reference.

In addition to the diagnostic and detection applications, therapeutic applications are also conceivable for the antibodies produced in this manner (A. N. Houghton, D. A. Scheinberg, *Semin. Oncol.* 13: 165–179 (1986); W. C.

Eckelmarm, *In Vivo Diagnosis and Therapy of Human Tumors with Monoclonal Antibodies;* Pergamon Press, London 1988; M. H. Ravindranath, D. L. Morton, R. F. Irie, *Cancer Res.* 49: 3891-3897 (1989)).

In another embodiment, the invention relates to a diagnostic kit for detecting a carbohydrate ligand that binds to a selectin. This kit comprises the antibody of the present invention. The kit may also comprise a detectable label and a set of written instructions for using such a kit. Such a kit may comprise a receptacle being compartmentalized to receive one or more containers such as vials, tubes and the like, such containers holding separate elements of the invention.

In another embodiment, the antibody of the invention is used in a method of detecting in a sample a carbohydrate ligand. This in vitro assay involves contacting a sample suspected of containing a-carbohydrate ligand-expressing cell with the above described antibody, which is detectably labeled. The carbohydrate ligand-expressing cell that binds to the antibody is then detected. By "sample" is meant any body fluid or tissue, including blood, urine, saliva, spinal fluid, semen, peritoneal fluid, and tissue from any part of the body, such as any organ, muscle or skin. A wide variety..of detectable labels may be used, and the antibody may be labeled by any one of several methods. A common method of detection is the use of autoradiography with $^3$H, $^{125}$I, $^{35}$S, $^{14}$C or $^{32}$P labeled compounds or the like. For instance, antibodies can be iodinated by contact with sodium or potassium iodide and a chemical oxidizing agent such as sodium hypochlorite, or an enzymatic oxidizing agent, such as lactoperoxidase. The choice of radioactive isotope depends on research preferences due to ease of synthesis, varying stability, and half lives of the selected isotopes.

Non-radioactive labels including fluorophores, chemiluminescent agents, and enzymes may be employed. The choice of label depends on sensitivity required, ease of conjugation with the compound, stability requirements, and available instrumentation. Non-radioactive labels are often attached by indirect means. Generally, a ligand molecule (e.g., biotin) is covalently bonded to the molecule. The ligand then binds to an anti-ligand (e.g., streptavidin) molecule which is either inherently detectable or covalently bound to a signal system, such as a detectable enzyme, a fluorescent compound, or a chemiluminescent compound. Ligands and anti-ligands may be varied widely.

This assay can be a competitive or sandwich assay, or any assay well-known to the artisan which depends on the formation of an antibody-antigen complex. For purposes of this invention, the antibody can be immobilized or labeled. Many carriers are known to the skilled artisan to which the antibody of the present invention can be bound for immobilization. Where required, derivatization techniques can be used for immobilizing the antibody on a substrate. Well-known carriers include glass, polystyrene, polypropylene, polyethylene, dextran, nylon, amylases, natural and modified celluloses, etc. The carrier can be either soluble or insoluble. Immunoassays encompassed by the present invention include, but are not limited to those described in U.S. Pat. No. 4,367,110 (double monoclonal antibody sandwich assay); Wide et al., Kirkham and Hunter, eds. *Radioimmunoassay Methods*, E. and S. Livingstone, Edinburgh (1970); U.S. Pat. No. 4,452,901 (western blot); Brown et al., *J. Biol. Chem.* 255: 4980-4983 (1980) (immunoprecipitation of labeled ligand); and Brooks et al., *Clin. Exp. Immunol.* 39: 477 (1980) (immunocytochemistry).

In another embodiment, the invention relates to a method of detecting in a sample a selectin-expressing cell. This in vitro assay involves contacting an above described sample suspected of containing a selectin-expressing cell with a compound according to the invention that is detectably labeled. The selectin-expressing cell that binds to the detectably labeled compound is then detected. By the term "selectin-expressing cell" is meant that a selectin is produced by a cell and that production can be detected by any known method, for instance, by direct assays of mRNA transcripts. Such cells include but are not limited to endothelial cells and various circulating cells of the hematolymphoid system. In certain assays, the "cell" may be a membrane preparation of a cell. Assays included in the present invention may involve flow cytometry and a fluorescence-activated cell sorter, according to methods well-known in the art. Parks et al., *Fund. Immunol.*, Paul, ed., Raven Press, 2d ed. (1989), which is incorporated herein by reference.

Other assays involve binding the compound of the present invention or the cells to be analyzed to a solid surface. Many methods for immobilizing biomolecules on solid surfaces are known in the art. For instance, the solid surface may be a membrane (e.g., nitrocellulose), a microtiter dish or a bead. The bound molecule may be covalently or noncovalently attached through unspecific bonding. The manner of linking a wide variety of compounds to various surfaces is well-known and well-documented in the literature. See, e.g., Chibata, *Immunological Enzymes*, Halsted Press (1978) and Cuatvecasos, *J. Bioi. Chem.* 245: 3059 (1970), which are incorporated herein by reference.

In the assay of the present invention for detecting selectin on selectin-expressing cells, the compound of the invention is labeled by methods well-known in the art. A common method involves the use of radioisotopes such as $^3$H, $^{125}$I, $^{35}$S, $^{14}$C or $^{32}$P. Detection is accomplished by autoradiography. Non-radioactive labels include the covalent binding of biotin to the compound of the present invention. Biotin is then bound to an anti-ligand such as streptavidin, which is either inherently labeled or bound to a signal system, such as a detectable enzyme, a fluorescent or chemiluminescent compound.

Without further elaboration, it is believed that one skilled in the art can, using the preceding description, utilize the present invention to its fullest extent. The following examples are merely illustrative and not limitative of the remainder of the disclosure in any way whatsoever.

EXAMPLE 1 a) Synthesis of 5-allyloxy-1-p-toluenesulfonyloxypentane (1a):

A mixture of pentanediol (21.8 ml, 207 mmol), allyl bromide (11.7 ml, 138 mmol), potassium carbonate (21 g, 151.8 mmol) and dibenzo-18-crown-6 is treated in an ultrasonic bath for 24 hours. It is then diluted with dichloromethane (250 ml) and washed twice with water (100 ml each). The organic phase is dried over magnesium sulfate and concentrated, and the residue is stirred with pyridine (50 ml, 600 mmol), dichloromethane (700 ml) and p-toluenesulfonyl chloride (40 g, 207 mmol). After 16 hours, the mixture is washed with saturated sodium chloride solution, and the organic phase is dried and concentrated. Flash chromatography (hexane/ethyl acetate 6:1→5:1) yields compound 1a (19.9 g, 53%)

$^1$H-NMR (300 MHz, CDCl$_3$): δ=1.39, 1.53, 1.66 (3m, 6H, —CH$_2$—CH$_2$CH$_2$—CH$_2$—), 2.45 (s, 3H, CH$_{3tos}$), 3.38 (t, 2H, OCH$_2$—), 3.93 (m, 2H, O—C$\underline{H}_2$—CH=CH$_2$), 4.01 (t, 2H, OCH$_2$—), 5.20 (m, 2H, O—CH$_2$—CH=C$\underline{H}_2$), 5.88 (m, 1H, O—CH$_2$—C$\underline{H}$=CH$_2$), 7.34, 7.78 (2m, 4H, tosyl-H$_{aromat}$).

b) Synthesis of 5-allyloxy-1-hydroxypentyl-(1→1)-(1R, 2R)-trans-1,2-cyclohexanediol (2a):

Sodium hydride (537 mg, 22.4 mmol) is added with stirring to a solution of (1R,2R)-trans-1,2-cyclohexanediol (Fluka, 3 g, 25.83 mmol) in DMF (75 ml). After 1 hour, compound 1a (4.7 g, 17.22 mmol) dissolved in a little DMF is added dropwise. After 18 hours, the mixture is diluted with dichloromethane (500 ml) and washed with water until the wash water has a neutral reaction. The organic phase is concentrated and the residue is purified by means of flash chromatography (hexane/ethyl acetate 4:1). Yield: 2.63 g, 63%.

$^1$H-NMR (300 MHz, CDCl$_3$): δ=2.82 (bs, 1H, OH), 3.00 (m, 1H), 3.96 (m, 2H, O—C$\underline{H}_2$—CH=CH$_2$), 5.22 (m, 2H, O—CH$_2$—CH=C$\underline{H}_2$), 5.90 (m, 1H, O—CH$_2$—C$\underline{H}$=CH$_2$).

c) Synthesis of 5-allyloxy-1-hydroxypentyl-(1→1)-[(2,3,4-tri-O-benzyl-α-L-fucopyranosyl)-(1→2)]-(1R,2R)-trans-1,2-cyclohexanediol (3a):

A mixture of 2a (4.6 g, 19 mmol), thioethyl-O-2,3,4-tri-O-benzyl-β-L-fucopyranoside (13.6 g, 28.51 mmol) and tetrabutylammonium bromide (1.4 g, 4.37 mmol) in dichloromethane (365 ml) and DMF (74 ml) is stirred with molecular sieve 4 A for 1 hour. Copper(II) bromide (7.6 g, 34.2 mmol) is then added. After 24 hours, the mixture is filtered through kieselguhr, and washed with saturated sodium hydrogen carbonate solution and then with saturated sodium chloride solution. The organic phase is dried over magnesium sulfate and concentrated in vacuo, and the residue is flash chromatographed (hexane/ethyl acetate 6:1). Yield: (11.9 g, 95%) of compound 3a.

$^1$H-NMR (300 MHz, CDCl$_3$): δ=1.10 (d, 3H, 6-H$_{fuc}$), 4.25 (q, 1H, 5-H$_{fuc}$), 5.18 (m, 2H, O—CH$_2$CH=C$\underline{H}_2$), 5.88 (m, 1H, O—CH$_2$—C$\underline{H}$=CH$_2$).

d) Synthesis of 5-hydroxy-1-hydroxypentyl-(1→1)-[(2,3,4-tri-O-benzyl-α-L-fucopyranosyl)-(1→2)]-(1R,2R)-trans-1,2-cyclohexanediol (4a):

A mixture of compound 3a (15.0 g, 22.78 mmol), Wilkinson catalyst (2.1 g, 2.3 mmol) and DBU (2.3 ml) is boiled under reflux for one hour in ethanol/water (9:1, 362 ml). It is then concentrated in vacuo and chromatographed through a short silica gel column (hexane/ethyl acetate 4:1). The enol ether is dissolved in acetone/water (9:1, 54 ml) and treated with mercury(II) oxide (8.3 g). Mercury (II) chloride (8.3 g, 30.75 mmol) dissolved in acetone/water (9:1, 166 ml) is added dropwise with stirring. After 1 hour, the mixture is filtered off with suction through kieselguhr, washed with chloroform (840 ml) and extracted by shaking with 30% strength potassium iodide solution (3×170 ml). The organic phase is dried over magnesium sulfate, concentrated and chromatographed (hexane/ethyl acetate 2:1→1:1). Yield: (9.53 g, 71%.

$^1$H-NMR (300 MHz, CDCl$_3$): δ=1.08 (d, 3H, 6-H$_{fuc}$), 4.24 (q, 1H, 5-H$_{fuc}$).

e) Synthesis of 5-p-toluenesulfonyloxy-1-hydroxypentyl—(1→1)-[(2,3,4-tri-O-benzyl-δ-L-fucopyranosyl)-(1→2)]-(1R,2R)-trans-1,2-cyclohexanediol (5a):

p-Toluenesulfonyl chloride (924 mg, 4.85 mmol) is added at 0° C. to a solution of compound 4a (2.0 g, 3.23 mmol) in pyridine (40 ml). After 18 hours, the mixture is diluted with dichloromethane (800 ml) and washed with saturated sodium chloride solution (2×200 ml) and the organic phase is dried over sodium sulfate and then concentrated at 25° C. Flash chromatography (hexane/ethyl acetate 5:1→4:1) yields compound 5a (1.66 g, 69%).

$^1$H-NMR (300 MHz, CDCl$_3$): δ=1.08 (d, 3H, 6-H$_{fuc}$), 2.42 (s, 3H, CH$_{3tosyl}$), 4.19 (q, 1H, 5-H$_{fuc}$), 4.94 (d, 1H, 1-H$_{fuc}$).

f) Synthesis of 5-dimethylmalonyl-1-hydroxypentyl-(1→1)-[(2,3,4-tri-O-benzyl-α-L-fucopyranosyl)-(1→2)]-(1R,2R)-trans-1,2-cyclohexanediol (6a):

A mixture of compound 5a (250 mg, 0.335 mmol), dimethyl malonate (0.3 ml, 2.6 mmol), potassium carbonate (0.18 g, 1.3 mmol) and dibenzo-18-crown-6 (47 mg, 0.13 mmol) in toluene (2 ml) is stirred at 100° C. for 24 hours. The mixture is chromatographed (hexane/ethyl acetate 5:1). Compound 6a (216 mg, 88%) is obtained.

$^1$H-NMR (300 MHz, CDCl$_3$): δ=1.09 (d, 3H, 6-H$_{fuc}$), 3.72 (2s, 6H, C(COOMe)$_2$), 4.22 (q, 1H, 5-H$_{fuc}$), 4.95 (d, 1H, 1-H$_{fuc}$).

g) Synthesis of 5-malonyl-1-hydroxypentyl-(1→1)-[(α-L-fucopyranosyl)-(1→2)]-trans-1,2-cyclohexanediol (7a):

A mixture of compound 6a (180 mg, 0.25 mmol) and palladium on carbon (10%, 180 mg) in methanol/dioxane (10:1, 44 ml) is hydrogenated under normal pressure in a hydrogen atmosphere for 24 hours. The palladium on carbon is filtered off, the filtrate is concentrated and the residue is treated with 1M sodium hydroxide solution (7 ml). After 2 hours, the mixture is neutralized with Amberlite IR-120 and purified through Biogel P-2. Compound 7a (100 mg., 92%) is obtained.

$^1$H-NMR (300 MHz, D$_2$O): δ=1.07 (d, 3H, 6-H$_{fuc}$), 1.2 (m, 6H, 4-H$_{cyclohex}$, 5-H$_{cyclohex}$, —CH$_2$—), 1.42, 1.55, 1.65, 1.96 (4m, 8H), 4.14 (q, 1H, 5-H$_{fuc}$), 4.91 (d, 1H, 1-H$_{fuc}$).

EXAMPLE 2 a) Synthesis of 3-allyloxy-1-p-toluenesulfonyloxypropane (1b):

Compound 1b is synthesized from propanediol analogously to compound 1a.

$^1$H-NMR (300 MHz, CDCl$_3$): δ=1.92 (m, 6H, —CH$_2$—), 2.45 (s, 3H, CH$_{3tos}$), 3.44 (t, 2H, OCH$_2$—), 3.87 (m, 2H, O—C$\underline{H}_2$—CH=CH$_2$), 4.15 (t, 2H, OCH$_2$—), 5.20 (m, 2H, O—CH$_2$—CH=C$\underline{H}_2$), 5.82 (m, 1H, O—CH$_2$—C$\underline{H}$=CH$_2$), 7.34, 7.79 (2m, 4H, tosyl-H$_{aromat}$).

b) Synthesis of 3-allyloxy-1-hydroxypropyl-(1→1)-(1R, 2R)-trans-1,2-cyclohexanediol (2b):

Compound 2b is synthesized analogously to 2a from 1b and (1R,2R)-trans-1,2-cyclohexanediol.

$^1$H-NMR (300 MHz, CDCl$_3$): δ=2.82 (bs, 1H, OH), 3.00 (m, 1H), 3.96 (m, 2H, O—C$\underline{H}_2$—CH=CH$_2$), 5.22 (m, 2H, O—CH$_2$—CH=C$\underline{H}_2$), 5.90 (m, 1H, O—CH$_2$—C$\underline{H}$=CH$_2$).

c) Synthesis of 3-allyloxy-1-hydroxypropyl-(1→1)-[(2,3,4-tri-O-benzyl-α-L-fucopyranosyl)-(1→2)]-(1R,2R)-trans-1,2,-cyclohexanediol (3b):

Compound 3b is synthesized analogously to compound 3a from 2b and thioethyl-O-2,3,4-tri-O-benzyl-β-L-fucopyranoside.

$^1$H-NMR (300 MHz, CDCl$_3$): δ=1.10 (d, 3H, 6-H$_{fuc}$), 4.23 (q, 1H, 5-H$_{fuc}$), 5.18 (m, 2H, O—CH$_2$—CH=C$\underline{H}_2$), 5.86 (m, 1H, O—CH$_2$—C$\underline{H}$=CH$_2$).

d) Synthesis of 3-hydroxy-1-hydroxypropyl-(1→1)-[(2,3,4-tri-O-benzyl-α-L-fucopyranosyl)-(1→2)]-(1R,2R)-trans-1,2-cyclohexanediol (4b):

Compound 4b is synthesized by deallylation of 3b corresponding to the synthesis of 4a.

$^1$H-NMR (300 MHz, CDCl$_3$): δ=1.09 (d, 3H, 6-H$_{fuc}$), 4.23 (q, 1H, 5-H$_{fuc}$).

e) Synthesis of 3-p-toluenesulfonyloxy-1-hydroxypropyl-(1→1)-[(2,3,4-tri-O-benzyl-α-L-fucopyranosyl)-(1→2)]-(1R,2R)-trans-1,2-cyclohexanediol (5b):

The tosylation of compound 4b is carried out analogously to the synthesis of 5a.

¹H-NMR (300 MHz, CDCl₃): δ=1.05 (d, 3H, 6-H$_{fuc}$), 2.41 (s, 3H, CH$_{3tosyl}$), 4.94 (d, 1H, 1-H$_{fuc}$).

f) Synthesis of 3-dimethylmalonyl-1-hydroxypropyl-(1→1)-[(2,3,4-tri-O-benzyl-α-L-fucopyranosyl)-(1→2)]-(1R,2R)-trans-1,2-cyclohexanediol (6b):

Compound 6b is synthesized analogously to compound 6a.

¹H-NMR (300 MHz, CDCl₃): δ=1.11 (d, 3H, 6-H$_{fuc}$), 3.69 (s, 6H, C(COOMe)₂), 4.21 (q, 1H, 5-H$_{fuc}$), 4.96 (d, 1H, 1-H$_{fuc}$).

g) synthesis of 3-malonyl-1-hydroxypropyl-(1→1)-[(α-L-fucopyranosyl)-(1→2)]-(1R,2R)-trans-1,2-cyclohexanediol (7b):

Compound 6b is deprotected analogously to 6a.

¹H-NMR (300 MHz, D₂O): δ=1.06 (d, 3H, 6-H$_{fuc}$), 1.06 (m, 4H, 4-H$_{cyclohex}$, 5-H$_{cyclohex}$), 1.47, 1.56, 1.76, 1.98 (4m, 8H), 4.13 (q, 1H, 5-H$_{fuc}$), 4.90 (d, 1H, 1-H$_{fuc}$).

EXAMPLE 3

Synthesis of 3-malonyl-1-hydroxybutyl-(1→1)-[(α-L-fucopyranosyl)-(1→2)]-(1R,2R)-trans-1,2-cyclohexanediol (7c):

Compound 7c is prepared analogously to compounds 7a and 7b.

EXAMPLE 4 a) Synthesis of [(2,3,4-tri-O-benzyl-α-L-fucopyranosyl)-(1→1)]-(1R,2R)-trans-1,2-cyclohexanediol (1d):

A mixture of (1R,2R)-trans-1,2-cyclohexanediol (2.43 g, 20.9 mmol), thioethyl-O-2,3,4-tri-O-benzyl-β-L-fucopyranoside (8.0 g, 16.72 mmol) and tetrabutylammonium bromide (2.7 g, 8.36 mmol) in dichloromethane (200 ml) and DMF (40 ml) is stirred with molecular sieve 4 Å for 1 hour. Copper(II) bromide (5.6 g, 25.08 mmol) is then added. After 24 hours, the mixture is worked up as described in 3a and chromatographed using hexane/ethyl acetate 3:1. Yield: (6.8 g, 76%).

¹H-NMR (300 MHz, CDCl₃): δ=1.13 (d, 3H, 6-H$_{fuc}$), 1.21 (m, 4H, 4-H$_{cyclohex}$, 5-H$_{cyclohex}$), 1.65, 2.01 (2m, 4H, 3-H$_{cyclohex}$, 6-H$_{cyclohex}$).

b) Synthesis of 1-hydroxy-4-aminocarbonylbutyl-(4→2)-[(2,3,4-tri-O-benzyl-α-L-fucopyranosyl)-(1→1)]-(1R,2R)-trans-1,2cyclohexanediol (2d):

Triethylamine (854 μl, 3.08 mmol), DMAP (38 mg, 0.308 mmol) and nitrophenyl chloroformate (1.128 g, 2.8 mmol) are added to a solution of 1c (1.5 g, 2.8 mmol) in dichloromethane (30 ml). The mixture is stirred overnight and treated with N-ethyldiisopropylamine (599 μl, 3.5 mmol) and 4-amino-1-butanol (325 μl, 3.5 mmol). The mixture is stirred again for 18 hours. For working up, it is diluted with dichloromethane (70 ml) and washed with water (3×30 ml). The organic phase is concentrated in vacuo and chromatographed with toluene/acetone 3:1. Yield: (1.4 g, 77%).

¹H-NMR (300 MHz, CDCl₃): δ=1.08 (d, 3H, 6-H$_{fuc}$), 1.30 (m, 4H, 4-H$_{cyclohex}$, 5-H$_{cyclohex}$), 1.53 (m, 4H, —CH₂—CH₂—), 1.65, 2.01 (2m, 4H, 3 -H$_{cyclohex}$, 6-H$_{cyclohex}$).

c) Synthesis of 4-malonyl-1-aminocarbonylbutyl-(4→2)-[(α-L-fucopyranosyl)-(1→1)]-(1R,2R)-trans-1,2-cyclohexanediol (3d):

Compound 3d is prepared analogously to compound 7a (four stages from 2d: tosylate, malonylate, hydrogenate, hydrolyse) with the difference that the reaction of the tosylate prepared from 2d with dimethyl malonate is carried out at 60° C. (5 hours). The hydrogenolysis of the benzyl groups proceeds completely analogously and the hydrolysis of the malonic ester is carried out in MeOH/1M aqueous NaOH 2:3 (2 hours).

¹H-NMR (300 MHz, D₂O): δ=1.08 (d, 3H, 6-H$_{fuc}$), 1.30 (m, 4H, 4-H$_{cyclohex}$, 5-H$_{cyclohex}$), 1.53 (m, 4H, —CH₂—CH₂—), 1.65, 2.01 (2m, 4H, 3-H$_{cyclohex}$, 6-H$_{cyclohex}$), 1.13 (m, 4H), 1.37 (m, 4H), 1.60 (m, 4H), 1.80, 2.01 (2m, 2H), 3.90 (q, 1H, 5-H$_{fuc}$), 4.49 (m, 1H, 2-H$_{cyclohex}$), 4.89 (bs, 1H, 1-H$_{fuc}$).

EXAMPLE 5 a) Synthesis of (1R, 2R)-trans-1,2-cyclohexanediol-O-2,3,4,6-tetra-O-acetyl-β-D-galactopyranoside (1e):

A 1M trimethylsilyl trifluoromethanesulfonate solution (2.3 ml) is added to a solution of O-(2,3,4,6-tetra-O-acetyl-D-galactopyranosyl) trichloroacetimidate (11.29 g, 22.9 mmol) and cyclohexanediol (4.0 g, 34.35 mmol) in dichloromethane/ether (100:200 ml). After 1 hour, the mixture is neutralized with sodium hydrogen carbonate (1 g), filtered and concentrated in vacuo. Chromatography of the residue (toluene/acetone 5:1) yields compound 1e (7.4 g, 72%).

b) Synthesis of (1R,2R)-trans-1,2-cyclohexanediol-O-(2,3,4-tri-O-benzyl-α-L-fucopyranosyl)-2,3,4,6-tetra-O-acetyl-β-D-galactopyranoside (2e):

Compound 2e is synthesized analogously to 3a.

c) Synthesis of (1R,2R)-trans-1,2-cyclohexanediol-O-(2,3,4-tri-O-benzyl-α-L-fucopyranosyl)-β-D-galactopyranoside (3e):

A solution of 2e (7.6 g, 8.8 mmol) in methanol (360 ml) is treated with a 2M methanolic sodium methoxide solution (1.4 ml). After 3 hours, the mixture is neutralized with Amberlite IR-120, filtered and concentrated, and the residue is chromatographed (dichloromethane/methanol 25:1→20:1). Compound 3e (6.0 g, 98%) is obtained.

d) Synthesis of (1R,2R)-trans-1,2-cyclohexanediol-O-(2,3,4-tri-O-benzyl-α-L-fucopyranosyl)-β-D-3-O-benzylgalactopyranoside (4e):

A solution of 3e (2 g, 2.88 mmol) and dibutyltin oxide (0.86 g, 3.45 mmol) in methanol (31 ml) is boiled under reflux. After 18 hours, the mixture is concentrated and coevaporated with toluene. The residue is dissolved in toluene (38 ml), treated with benzyl bromide (3.5 ml, 29.9 mmol) and tetrabutylammonium iodide (1.34 g, 3.63 mmol) and warmed to 45° C. After 3 hours, the mixture is concentrated and the residue is chromatographed using dichloromethane/methanol 25:1. Yield: (1.6 g, 71%).

¹H-NMR (300 MHz, CDCl₃): δ=1.09 (d, 3H, 6-H$_{fuc}$), 2.48 (d, 1H, OH), 2.55 (bs, 1H, OH), 4.30 (d, 1H, 1-H$_{gal}$).

e) Synthesis of (1R,2R)-trans-1,2-cyclohexanediol-O-(2,3,4-tri-O-benzyl-α-L-fucopyranosyl)-β-D-3-O-benzyl-4,6-O-benzylidene-galactopyranoside (5e):

Benzaldehyde dimethyl acetal (0.44 ml, 2.94 mmol) and p-toluenesulfonic acid (84 mg) are added to a solution of 4e (1.16 g, 1.47 mmol) in acetonitrile (63 ml). After 1 hour, the reaction is stopped with potassium carbonate (1 g), the mixture is filtered and concentrated, and the residue is chromatographed using hexane/ethyl acetate (3:1→2:1→1:1). Compound 5e (1.14 g, 89%) is obtained.

¹H-NMR (300 MHz, CDCl₃): δ=1.03 (d, 3H, 6-H$_{fuc}$), 2.39 (d, 1H, OH), 5.50 (s, 1H, CHPh).

f) Synthesis of (1R,2R)-trans-1,2-cyclohexanediol-O-(α-L-fucopyranosyl)-β-D-2-O-malonylethylgalactopyranoside (6e):

Compound 6e is synthesized as described in 7a (alkylation with 2-allyloxy-1-p-toluenesulfonyloxyethane, deallylation, tosylation, malonylation, hydrogenolysis, hydrolysis).

$^1$H-NMR (300 MHz, D$_2$O): δ=1.04 (d, 3H, 6-H$_{fuc}$), 4.38 (d, 1H, 1-H$_{gal}$), 4.45 (q, 1H, 5-H$_{fuc}$), 4.86 (d, 1H, 1-H$_{fuc}$).

EXAMPLE 6 a) Synthesis of 4,6-isopropylidene-1,2-didesoxyglucose (1f):

A solution of tri-O-acetyl-D-glucal (30 g, 110.17 mmol) in dioxane (400 ml) is hydrogenated with palladium on carbon (10%, 3 g) for 24 hours in a hydrogen atmosphere. The mixture is filtered through kieselguhr and concentrated. To remove the acetyl groups, the residue is taken up in methanol (500 ml) and a 1M sodium methoxide solution (6 ml) is added. After 90 minutes, the mixture is neutralized with Amberlite IR-120, filtered and concentrated in vacuo. The residue is coevaporated with toluene (3×250 ml) and taken up in DMF (500 ml). Dimethoxypropane (140 ml, 114.6 mmol) and p-toluenesulfonic acid (400 mg) are added to the solution. After 18 hours, triethylamine (3 ml) is added, and the mixture is stirred for a further 15 minutes and concentrated in a high vacuum. Chromatography (toluene/acetone 4:1) yields compound if (33 g, 80%).

$^1$H-NMR (300 MHz, CDCl$_3$): δ=1.41, 1.51 (2s, 6H, 2 CH$_3$), 1.76 (ddd, 1H, 2-H), 2.0 (ddd, 1H, 2-H), 2.8 (d, 1H, OH), 3.16 (m, 1H, 1-H), 3.46 (dd, 1H, 6-H), 3.53 (m, 1H, 1-H), 3.7 (dd, 1H, 6-H), 3.86 (dd, 1H, 4-H), 3.96 (m, 1H, 5-H).

b) Synthesis of 4-allyloxy-1-hydroxybutyl-(1→3)-4,6-isopropylidene-1,2-didesoxyglucose (2f):

2f is synthesized analogously to 2a.

c) Synthesis of 4-allyloxy-1-hydroxybutyl-(1→3)-1,2-didesoxyglucose (3f):

Twenty percent strength trifluoroacetic acid (30 ml) is added to a solution of 2a (4.17 g, 14 mmol) in dichloromethane (340 ml). After 4 hours, toluene (200 ml) is added to this and it is concentrated to a half. Toluene is added to the mixture again and it is concentrated. The residue is chromatographed (dichloromethane/methanol 50:1→40:1→30:1). Compound 3f (3.26 g, 90%) is obtained.

$^1$H-NMR (300 MHz, CDCl$_3$): δ=1.53 (ddd, 1H, 2-H), 1.66 (m, 4H, CH$_2$CH$_2$), 2.0 (ddd, 1H, 2-H), 2.9 (bs, 1H, OH), 5.22 (m, 2H, O—CH$_2$—CH=CH$_2$), 5.9 (m, 1H, O—CH$_2$—CH=CH$_2$).

d) Synthesis of 4-phenyl-1-1-trifluoromethanesulfonyloxybutane (4f):

A mixture of 4-phenyl-1-butanol (3 ml, 20 mmol), pyridine (1.6 ml, 20 mmol) and dichloromethane (10 ml) is added dropwise with stirring to an ice-cold solution of trifluoromethanesulfonic anhydride (3.8 ml, 23 mmol) in dichloromethane (35 ml). After 1 hour, dichloromethane (65 ml) is added and the mixture is washed with water (3×20 ml), dried over magnesium sulfate and concentrated in vacuo at 25° C. The residue is chromatographed (hexane/ethyl acetate 7:1). Compound 4f (3.8 g, 70%) is obtained.

$^1$H-NMR (300 MHz, CDCl$_3$): δ=1.84 (m, 4H, —CH$_2$—CH$_2$—), 2.67 (t, 2H, —CH$_2$—Ph), 4.52 (t, 2H, —CH$_2$—OTf), 7.24 (m, 5H, Ph).

e) Synthesis of 4-allyloxy-1-hydroxybutyl- (1→3)-[4-phenyl-1-hydroxybutyl-(1→6)]-1,2-didesoxyglucose (5f):

A mixture of 3f (850 mg, 3.3 mmol), 4f (1.21 g, 4.3 mmol), potassium carbonate (684 mg, 4.95 mmol) and dibenzo-18-crown-6 (174 mg, 480 mmol) is stirred in toluene (14 ml) for 18 hours. For working up, the mixture is filtered and chromatographed (toluene/acetone 10:1). Yield: (942 mg, 73%).

$^1$H-NMR (300 MHz, CDCl$_3$): δ=1.53 (ddd, 1H, 2-H), 1.66 (m, 8H, 4 CH$_2$), 2.00 (m, 1H, 2-H), 2.60 (dd, 2H, CH$_2$Ph), 2.87 (bs, 1H, OH), 3.95 (m, 2H, O—CH$_2$—CH=CH$_2$), 5.22 (m, 2H, O—CH$_2$—CH=CH$_2$), 5.91 (m, 1H, O—CH$_2$—CH=CH$_2$).

f) Synthesis of 4-allyloxy-1-hydroxybutyl-(1→3)-[(2,3,4-tri-O-benzyl-α-L-fucopyranosyl)-(1→4)]-[4-phenyl-1-hydroxybutyl-(1→6)]-1,2-didesoxyglucose (6f):

The fucosylation is carried out as described in 3a.

g) Synthesis of 4-malonyl-1-hydroxybutyl-(1→3)-[(α-L-fucopyranosyl)-(1→4)]-[4-phenyl-1-1-hydroxybutyl-(1→6)]-1,2-didesoxyglucose (7f):

7f is synthesized analogously to 7a (5 stages from 6f: deallylate, tosylate, malonylate, hydrogenate, hydrolyze).

$^1$H-NMR (300 MHz, D$_2$O): δ=1.0 (d, 3H, 6-H$_{fuc}$), 2.50 (t, 2H, CH$_2$Ph), 2.90 (t, 2H), 4.20 (q, 1H, 5-H$_{fuc}$), 4.70 (d, 1H, 1-H$_{fuc}$).

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application Nos. P 44 08 248.7 (filed Mar. 11, 1994) and P 44 30 005.0 (filed Aug. 25, 1994) for which benefit under 35 USC §119 is claimed, are expressly incorporated herein in their entirety.

What is claimed is:

1. A compound of formula I

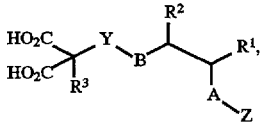

in which

R$^1$, R$^2$ and R$^3$ independently of one another are H, (CH$_2$)$_m$X or CH$_2$O(CH$_2$)$_m$X$^1$ or R$^1$ and R$^2$ together form a six-membered carbo- or heterocycle having at least one substituent selected from the group consisting of R$^4$, R$^5$ and R$^6$ and A and B independently of one another are O, S, NH, HN—CO, OC—NH, O—CO, OC—O, NH—CO—O, O—CO—NH, S—CO, SC—O, O—CS—S, S—CS—O, NH—CS—S, S—CS—NH or CH$_2$ and Z is a pyranose, a furanose, an open-chain polyalcohol or Y-X$^6$, Y is —O—(CX$_2$X$^3$)$_n$—, —(CX$^2$X$^3$)$_n$—, —(CX$^2$R$^7$)$_n$—, —(CR$^7$R$^8$)$_n$—, —CH$_2$—(CX$^2$X$^3$)$^-_n$ or a saturated or unsaturated, six-membered carbocycle or heterocycle having at least one substituent R$^9$, or Y is a pair of said carbocycle or said heterocycle and a chain, wherein said chain is selected from the group consisting of —O—(CX$^2$X$^3$)$_n$—, —(CX$^2$X$^3$)$_n$—, —(CX$^2$R$^7$)$_n$—, and —(CR$^7$R$^8$)$_n$—, where R$^4$, R$^5$ and R$^6$ independently of one another are H, OH, (CH$_2$)$_q$X$^4$, CH$_2$O(CH$_2$)$_q$X$^5$ or HNC(O)CH$_3$ and R$^7$, R$^8$ and R$^9$ independently of one another are H, OH, —O—(CH$_2$)$_q$X$^4$ or CH$_2$O(CH$_2$)$_q$X$^5$ and X, X$^1$, X$^2$, X$^3$, X$^4$ and X$^5$ independently of one another are H, NH$_2$, COOH, OH, CH$_2$OH, CH$_2$NH$_2$, C$_1$–C$_{20}$-alkyl or C$_6$–C$_{10}$-aryl and $X^6$ is OH or

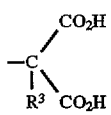

and m, n and q independently of one another is an integer from 1 to 20.

2. The compound of claim 1, wherein
$R^1$ and $R^2$ form a six-membered carbocycle and
$R^3$, $R^4$, $R^5$ and $R^6$ are H,
A is O,
Z is a -fucopyranosyl group,
Y is $(CX^2X^3)_n$ and
$X^2$ and $X^3$ are H.

3. The compound of claim 2, wherein B is O.
4. The compound of claim 3, wherein n is 3.
5. The compound of claim 3, wherein n is 4.
6. The compound of claim 3, wherein n is 5.
7. The compound of claim 2, wherein B is HNCO—O.
8. The compound of claim 7, wherein n is 4.
9. The compound of claim 1, wherein
$R^1$ and $R^2$ together form a six-membered carbocycle and
$R^3$, $R^4$, $R^5$ and $R^6$ are H,
A and B are 0,
Z is a fucopyranosyl group,
Y is a pair of a chain —O—$(CX^2X^3)_n$ and a heterocycle, where
$X^2$ and $X^3$ are H.

10. The compound of claim 9, wherein the heterocycle is a galactosyl radical and n is 2.
11. The compound of claim 1, wherein $R^1$ and $R^2$ together form a substituted tetrahydropyran ring,
A and B are O,
Z is a -fucopyranosyl group,
Y is $(CX^2X^3)_n$, where
$R^3$, $X^2$ and $X^3$ are H and n is 4.

12. The compound of claim 11, wherein $R^4$ and $R^5$ are H and $R^6$ is the ring substituent in the tetrahydropyran ring between the ring heteroatom O and the ring substituent -A-Z, and wherein $R^6$ is $CH_2O(CH_2)_qX^5$ and $X^5$ is $C_6H_5$.
13. The compound of claim 12, wherein q is 4.
14. The compound of claim 11, wherein the tetrahydropyran ring is a pyranose.

15. The compound of claim 12, wherein the pyranose is N-acetyl-D-glucosamine.

16. The compound of formula I of claim 1, wherein
$R^1$ and $R^2$ together form a six-membered carbocycle,
A-Z is

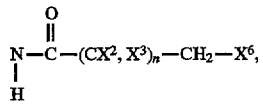

-B-Y is

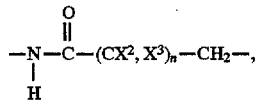

$R^3$ and $X^2$ are H,
$X^3$ and $X^6$ are OH and
n is 4.

17. The compound of claim 16, wherein $X^6$ is

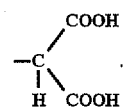

18. A pharmaceutical composition for inhibiting the binding of a selectin to a carbohydrate ligand on a cell expressing said carbohydrate ligand, said composition comprising a compound of formula I of claim 1 in a pharmaceutically acceptable carrier.

19. A method of inhibiting the binding of a selectin to a carbohydrate ligand on a cell expressing said carbohydrate ligand, comprising the step of administering to a subject suffering from a selectin-mediated disease a therapeutically effective dose of the pharmaceutical composition of claim 18.

20. The method of claim 19, wherein said cell expressing said carbohydrate ligand is selected from the group consisting of a bacteria, a virus, a white blood cell and a cancer cell.

* * * * *